United States Patent [19]
Lin

[11] Patent Number: 5,857,957
[45] Date of Patent: Jan. 12, 1999

[54] FUNCTIONAL MAGENTIC STIMULATION OF THE EXPIRATORY MUSCLES

[76] Inventor: Vernon Wen-Hau Lin, 1620 Albatross, Sunnyvale, Calif. 94087

[21] Appl. No.: 811,535

[22] Filed: Mar. 4, 1997

[51] Int. Cl.⁶ .................................................. A61N 1/00
[52] U.S. Cl. .............................................................. 600/13
[58] Field of Search ........................ 600/13, 14; 607/155

[56] References Cited

U.S. PATENT DOCUMENTS

| | | | |
|---|---|---|---|
| 2,476,645 | 7/1949 | Wanzenberg | 607/155 |
| 3,841,305 | 10/1974 | Hallgren | 600/13 |
| 4,940,453 | 7/1990 | Cadwell | 600/13 |
| 5,066,272 | 11/1991 | Eaton et al. | 600/14 |

*Primary Examiner*—William E. Kamm
*Attorney, Agent, or Firm*—Forrest Collins

[57] ABSTRACT

Described herein is a device for inducing a cough function in a mammalian subject through electromagnetic induction. Also described herein is a method of treatment which provides a procedure which is non-invasive to individuals to stimulate cough functions in individuals including those individuals such as quadraplegic patients and in patients suffering from multiple sclerosis.

21 Claims, 1 Drawing Sheet

FUNCTIONAL MAGENTIC STIMULATION OF THE EXPIRATORY MUSCLES

BACKGROUND OF THE INVENTION

1. Field of the Invention.

This invention deals with the treatment of respiratory difficulty arising from an inability to at least partially eliminate sputum or secretions from the airway of a mammalian subject. The treatment of such respiratory difficulties typically arises in patients having limited spinal nervous function such as from quadriplegia or multiple sclerosis.

2. Description of the Art Practices.

In a normally functioning mammalian subject the breathing function occurs automatically with a periodic cough reflex when the subject senses the build up sputum or secretions in the airway. The sputum or secretions in the airway are the result from the normal operation of the mucosa in lubricating the airway and in trapping foreign material.

However, if the sputum or secretions are not periodically removed it will impair the subjects ability to obtain air through the airway. Secondly, if the build up of the sputum or secretions in the airway is sufficient it may result in complete blockage of the airway leading to asphyxia of the subject.

In U.S. Pat. No. 3,658,651 issued Apr. 25, 1972 to Maclean there is discussed a method of treatment by placing a patient or an animal to be treated between the poles of an electromagnet. The patient or an animal is then subjected to an a pulsating magnetic field induced by an intermittent direct current to the electromagnet with the peak intensity of each pulse being at least 2,000 gauss. The Maclean patent discusses as potential effects of his treatment the clearing of the stimulation of the endocrine glands, relief of pain, suppression of cough, and pleural effusion, energizing effects, clearing of the sensorium, relaxation of muscle spasm, development of peace of mind, and sense of well being, and increase of libido.

Linder in U.S. Pat. No. 5,190,036 issued Mar. 2, 1993 teaches an abdominal binder comprising an electrode belt for stimulating cough in a quadriplegic patient. Linder further discusses stimulating cough in a quadriplegic patient *Chest* Volume 103 number 1 January 1993 pages 166–199 article entitled Functional Electrical Stimulation to Enhance Cough in Quadriplegia.

Mouchawar, in an article entitled Closed-Chest Cardiac Stimulation with a Pulsed Magnetic Field, *Medical & Biological Engineering & Computing* March 1992, page 162 discusses magnetic stimulator to generate intense, rapidly changing magnetic fields capable of stimulating nerves. Magnetic resonance systems utilizing coplanar coils to provide a pulsed magnetic field with an average of 12 kilojoules to achieve closed-chest magnetically induced ectopic beats. The Mouchawar article also describes the peak-induced electrical field for threshold stimulation at 213 V/m for a 571 micro-second damped sine wave pulse.

Mouchawar et al., in an article entitled Magnetic Electrophrenic Nerve Stimulation to Produce Inspiration, published in the *Annals of Biomedical Engineering,* Volume 19, 1991 pages 219–221 discusses producing inspiration in a dog. The induced inspiration reported by Mouchawar et al. is plotted by integrating the inspiratory air-flow velocity record.

The author of the present patent published a note in entitled Magnetic Stimulation of the Intercostal Muscles at page 1237 of the Archives of Physical Medicine and Rehabilitation volume 74, November 1993. The present author has contributed to a note entitled the High Frequency Magnetic Stimulation of the Inspiratory Muscles which was published in *Muscle & Nerve* October 1993 Volume 16 number 10 at page 1088.

Manual methods of aiding respiration are discussed in U.S. Pat. No. 4,977,889 issued Dec. 18, 1990 to Budd. In the Budd patent a vest is utilized to stimulate respiration.

In a paper entitled Thoracic Spinal Nerve and Root Conduction: A Magnetic Stimulation Study Magnetic Stimulation of the Thoracic Nerves is discussed by Chokroverty et al. The Chokroverty et al. article was published in *Muscle & Nerve* September 1995 Volume 18, number 10 at pages 987–991.

Percutaneous magnetic stimulation is discussed in an article entitled Ventilatory Effects of Percutaneous Magnetophrenic Stimulation by Nagano et al. The Nagano et al. article was published in the *Frontiers of Medical Biological Engineering,* Volume 3, Number 2, pages 97–112 in 1991. An article entitled Cough in Spinal Cord Injured Patients: Comparison of Three Methods to Produce Cough was published by Jaeger et al. in the *Archives of Physical Medical Rehabilitation* Volume 74, December 1993 at pages 1358–1361. The Jaeger article, discusses various methods of phrenic nerve stimulation. Jaeger discloses artificial cough reflex stimulation in U.S. Pat. No. 5,314,454 issued May 24, 1994.

The effect of lung volume on transdiaphrematic pressure is discussed in an article by Hamnegard et al. The Hamnegard et al. article appears in the *European Respiratory Journal* 1995 Volume 8, pages 1532–1536.

Voorhees III et al., in a technical note in the *Journal of Clinical Engineering* September/October 1990 page 407 entitled Magnetically Induced Contraction of the Inspiratory Muscles in Dog discusses short-duration inspirations by discharging a capacitor bank into an excitation coil placed over the lower right chest. The Voorhees III article discusses utilizing the construction of the excitation coil as having 59 turns of ¼ inch copper ribbon 0.0200 inches thick wound on a ¾" diameter plastic rod where the outer diameter of the coil is 3.75" and the entire coil is potted in silicon rubber.

The inductance per Voorhees III et al. is 139 micro-H and the resistance is 0.084 ohms. The current was delivered to the coil from a 100-micro F capacitor bank. The resonant frequency of the system was 1350 Hz and the damping coefficient was 0.05.

Cadwell Laboratories, Inc. in Application Notes AP-2 Rev. 1 Feb. 22, 1990, discusses high speed magnetic stimulator characteristics.

In an article entitled Developing a More Focal Magnetic Stimulator Part I: Some Basic Principals by Cohen et al., as recorded in *Journal of Clinical Neurophysiology,* 8 (1); 102–111 (1991) magnetic stimulation is discussed generally. Similar disclosures are made by Yunokuchi et al. in the *Journal of Clinical Neurophysiology,* 8 (1); 112–120 (1991) in an article entitled Developing a More Focal Magnetic Stimulator. Part II: Fabricating Coils and Measuring Induced Current Distributions.

The reader is also referred to *Magnetic Stimulation in Clinical Neurophysiology* edited by Sudhansu Chokroverty and published by Butterworths, Boston, London, Singapore, Sydney, Toronto, and Wellington Chapter 3 pages 17 through 32, pages showing FIGS. 7-18; 14-1; 17-4; 17-10, 18-3 and 18-4.

Further reference is made to Magnetic Brain Stimulation With a Double Coil: The importance of Coil Orientation by Mills et al. published in *Electroencephalography and Clinical Neurophysiology,* 85 (1992) pages 17–21. Reference is also made to a publication entitled the Effects of Coil Design on Delivery of Focal Magnetic Stimulation-Technical Considerations Cohen et al., in *Electroencephalography and Clinical Neurophysiology,* 75 (1990) pages 350–357.

The assessment of nerve and muscle function is discussed in a paper entitled Comparison of Cervical Magnetic Stimulation and Bilateral Percutaneous Electrical Stimulation of the Phrenic Nerves in Normal Subjects as reported in *European Respiratory Journal* 1994 Volume 7, pages 1788–1702

A summary of the results presented in this patent was submitted for publication entitled Functional Magnetic Stimulation of The Expiratory Muscles for Cough by Lin et al.

To the extent that the foregoing references are relevant to the present invention, they are herein specifically incorporated by reference. Where temperatures are given, they are in degrees C unless otherwise indicated. Pressure measurements are reported in centimeters of water. Percentages and ratios given herein are by weight unless otherwise indicated. Measurements herein are stated in degrees of approximation and where appropriate the word "about" may be inserted before any measurement.

SUMMARY OF THE INVENTION

The present invention is directed to a method for treating a mammalian subject to induce pulmonary expiration including the steps of exposing the mammalian subject to sufficient electro-magnetic induction for a sufficient period of time to stimulate at least one of the T3 through L5 nerves of the mammalian subject to thereby induce the pulmonary expiration.

The present invention also provides a method for treating a mammalian subject to induce pulmonary expiration including the steps of exposing the mammalian subject to sufficient electromagnetic induction for a sufficient period of time to simulate at least one of the T3 through L5 nerves of the mammalian subject and to thereby induce the pulmonary expiration wherein the maximum radiation strength per electromagnetic induction is from 1 to 50 microcurie per electromagnetic induction and wherein the electro-magnetic induction is employed for 0.25 to 30 seconds.

Also described herein is a device for treating a mammalian subject to induce pulmonary expiration comprising:
  a functional electro-magnetic stimulator;
  said functional electro-magnetic stimulator having at least one coil wherein the coil is of a design to allow said coil to be hand held or directly placed on the mammalian subject;
  said coil having cooling means, for when the functional electromagnetic stimulator is operating to induce pulmonary expiration, to conduct heat generated in the coil from the coil.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

With more particular reference to the drawings the following is set forth.

DETAILED DESCRIPTION OF THE INVENTION

As previously discussed the invention deals with a non-physically invasive method to stimulate the rapid pulmonary expiration also known as cough. The present invention is directed to artificially stimulating cough in a mammalian subject requiring such cough stimulation.

In the present invention the cough function is stimulated with a functional electromagnetic stimulator. The equipment utilized for the functional electro-magnetic stimulation (electro-magnetic induction) of the cough function is conveniently available as a Dantec MagPro Magnetic Stimulator having a round coil 13.5 centimeters in diameter. A further functional electromagnetic stimulator useful in the present invention is the Cadwell HS M E S-10 Magnetic Stimulator 12 which is available from Cadwell Laboratories, Inc. 909 N. Kellogg Street, Kennewick, Wash. 99336. In any event, any suitable electromagnetic stimulation device may be utilized in the present invention.

Figure 1:
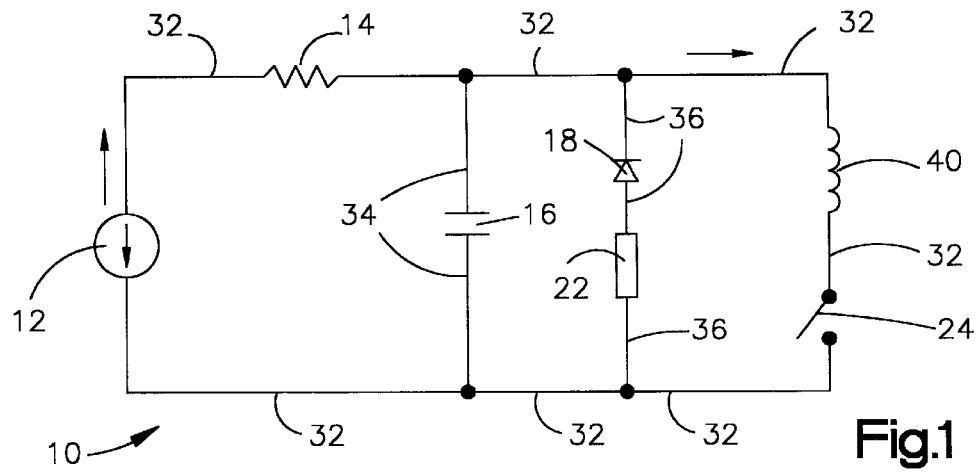
FIG. 1 shows the basic electronic design of a functional electromagnetic stimulator.

A functional electromagnetic stimulator 10 (FIG. 1) includes a charging circuit 12, a switch 14, and a capacitor 16. The functional electro-magnetic stimulator 10 further comprises a diode 18 and a resistor 22. A second switch 24 and a stimulation coil assembly 40 are also present in the functional electromagnetic stimulator 10.

Figure 2:
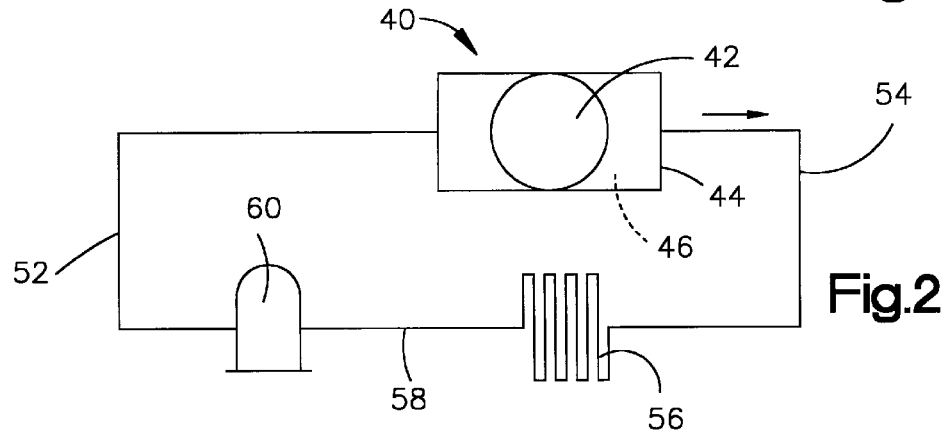
FIG. 2 shows an enlargement of a section of the functional electromagnetic stimulator of FIG. 1 including a cooling system for the coil of the functional electromagnetic stimulator.

The functional electromagnetic stimulator 10 is wired via a wire 32 in series from the charging circuit 12 to the switch 14. From the switch 14 the wire 32 continues to the stimulation coil assembly 40. Within the stimulation coil assembly 40, wire 32 makes contact with the circular coil 42 (FIG. 2).

The wire 32 continues from the circular coil 42 to switch 24 and completes the series circuit to the charging circuit 12. A wire 34 connects through the capacitor 16 to the wires 32 on both sides of the charging circuit 12.

A wire 36 connects from wire 32 to the resistor 22 in series. The wire 36 continues in series from the resistor 22 to the diode 18. The wire 36 connects from the diode 18 in series to the wire 32.

The capacitor 16 bridges the wires 32 between the charging circuit 12 and the stimulation coil assembly 40. The resistor 22 and the diode 18 bridges the wires 32 between the charging circuit 12 and the stimulation coil assembly 40. The capacitor 16 bridges the wires 32 between the charging circuit 12 and the resistor 22 and the diode 18. The direction of current flow through the wires 32 is shown by the arrow in FIG. 1.

The stimulation coil assembly 40 is shown in greater detail in FIG. 2. The stimulation coil assembly 40 includes a coil housing 44. Within the coil housing 44 is a chamber 46. Proximate the chamber 46 is the circular coil 42. For convenience, the wiring is not shown within the coil housing 44. Communicating with the chamber 46 within the coil housing 44 is an input line 52 for the transmission of a fluid (not shown).

Also communicating with the chamber 46 within the coil housing 44 is an exhaust line 54. The coil housing 44 is constructed to permit fluid flow through the chamber 46 from the input line 52 to exhaust line 54 which receives the fluid. The exhaust line 54 communicates with a heat exchanger 56. Fluid flow in a known manner is permitted from the exhaust line 54 to, and through, the heat exchanger 56. For convenience the direction of fluid flow through the exhaust line 54 is shown by the arrow in FIG. 2.

A transmission line 58 permits fluid flow from the heat exchanger 56 to a compressor 60. The compressor 60 in a known manner, when activated, compresses a fluid within the compressor 60. The compressor 60, when activated to compress the fluid, delivers the compressed fluid to the input line 52.

Figure 3:
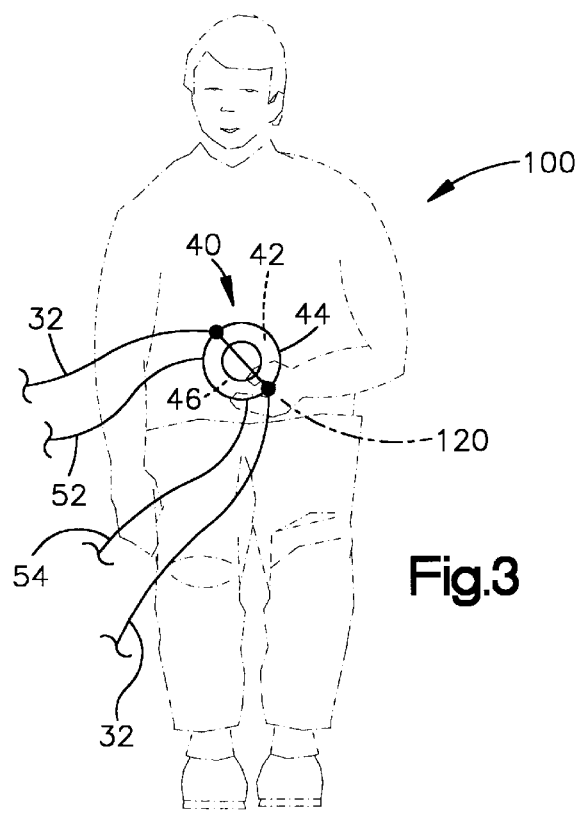
FIG. 3 shows functional electro-magnetic stimulation utilizing a magnetic coil where the magnetic coil portion of the functional electromagnetic stimulator, capable of being hand held, is applied in close proximity to a human subject.

A mammalian subject (human) 100 is shown in FIG. 3. The mammalian subject 100 is in a seated position on a stool (not shown). The stimulation coil assembly 40 is positioned such that an outer surface of the coil housing 44 is contacting the skin of the mammalian subject 100. The stimulation coil assembly 40 in the coil housing 44 is held by a hand 120 as shown in FIG. 3. In the foregoing manner the mammalian subject 100 is not subjected to adverse temperature conditions. The functional electromagnetic stimulator 10 is activated as later described to induce the cough function in the mammalian subject 100.

The current flow from the line 32 is to the circular coil 42 within the stimulation coil assembly 40. The current induces magnetic flux in the circular coil 42 for delivery to the mammalian subject 100. As a byproduct of inducing the magnetic flux heat energy is produced in vast quantities.

The input line 52 supplies coolant fluid, preferably a compressed gas such as R132A an environmentally friendly fluorocarbon refrigerant, to the stimulation coil assembly 40. Within the stimulation coil assembly 40 the fluid is permitted to flow in the chamber 46 drawing heat energy generated by the circular coil 42 thereby forming a heated fluid. The heated fluid exits the stimulation coil assembly 40 to the exhaust line 54.

The heated fluid in the exhaust line 54 flows, while dissipating some of the heat energy, to the heat exchanger 56. In the heat exchanger 56 the heated fluid is permitted to expand and/or to contact a surface cooler that the temperature of the heated fluid. The fluid now of at reduced temperature flows from the heat exchanger 56 to the transmission line 58.

The fluid in the transmission line 58 flows, while continuing to cool, to the compressor 60. Within the compressor 60 the fluid is compressed to a reduced volume for delivery to the input line 52.

The general parameters for treating a mammalian subject are to expose the mammalian subject to a field strength between 1 Hertz and 150 Hertz, preferably 3 Hertz to 100 Hertz and more preferably 10 Hertz to 40 Hertz. The duration of the electromagnetic induction stimulation provided is typically for 0.25 to 30 seconds, often 0.5 to 15 seconds, or 0.75 to 8 seconds.

To approximate normal cough function, the electromagnetic induction may be employed in repeated intervals. The intervals may conveniently correspond to 2 to 100 electromagnetic inductions per minute, typically 2 to 50 per minute, and often 6 to 25 per minute.

The following definitions are utilized to assist in an understanding of this invention. The foregoing definitions are largely drawn from Chapter 34, Pulmonary Function in the, *Review of Medical Physiology* authored by William F. Ganong, M. D., Copyright 1985 Lange Medical Publications, Los altos, Calif., 94023.

The tidal volume is the amount of air that moves into the lungs with each inspiration, or conversely, that amount of air that moves out of the lungs with each expiration. The inspiratory reserve volume is the amount of air inspired into the lungs by a maximal inspiratory effort in excess of the tidal volume.

The expiratory reserve volume is the volume of air expelled from the lungs after air is expelled from the lungs by an active expiratory effort. The amount of air left in the lungs after a maximal expiratory effort is the residual volume.

The vital capacity of the lungs is the greatest amount of air that can be expired after a maximal inspiratory effort. The forced vital capacity per unit of time is the amount of air that can be expired in a given period of time. The forced vital capacity per one minute of testing is refereed to as the FEV1. The term timed vital capacity for one minute is the same as the FEV1.

The forced vital capacity is the amount of air that can be expired in a given period of time. The forced vital capacity is typically measured in liters per second. The forced vital capacity is also referred to as the forced expiratory volume.

The total lung capacity is that amount of air obtained by the addition of the inspiratory reserve volume, the tidal volume, and the expiratory reserve volume and the reserve volume. The total lung capacity depends upon the size of the individual and in humans is expected to be about 5.5 to 7.5 liters for an adult male. The total volume in humans is expected to be about 4.5 to 6.0 liters for an adult female.

In the present invention it is desired that the stimulation of the cough in a subject be obtained as expressed in terms of maximal expired pressure and in forced expiratory flow rate both as determined at the end of a normal inspiration followed by the electromagnetic induction. However, the electro-magnetic induction of the subject may conducted at any point in the respiration cycle but is preferably conducted at the end of the inspiration cycle.

As the lung measurements described above will fluctuate depending upon the gender, age, general health, and even the number of lungs, the amount of air flow per cough and flow rate can only be generalized. A Medical Graphics respiratory pressure module and heated pneumatach are conveniently utilized in the measurement of the lung capacities.

The cough response will, as determined at the end of a normal inspiration followed by the electromagnetic induction, result in the expulsion of air at a pressure of at least about 10 centimeters of water. Preferably, the cough response will, as determined at the end of a normal inspiration followed by the electro-magnetic induction, result in the expulsion of air at a pressure of at least about 20 centimeters of water.

More preferably, the cough response will, as determined at the end of a normal inspiration followed by the electromagnetic induction, result in the expulsion of air at a pressure of at least about 50 centimeters of water. Yet more preferably, the cough response will, as determined at the end of a normal inspiration followed by the electro-magnetic induction, result in the expulsion of air at a pressure of at least about 100 centimeters of water.

Typically, the desired cough response will be, as determined at the end of a normal inspiration followed by the electro-magnetic induction results in the expulsion of air of at least 10% of the total lung capacity, preferably at least 15%, more preferably at least 30% and most preferably at least 40% of the total lung capacity.

The rate of expulsion of the air from the lungs per the desired cough response will be, as determined at the end of a normal inspiration followed by the electro-magnetic induction, results in the a rate of expulsion of the air of at least about 25 per cent of total lung capacity per second, preferably at least about 40 per cent of total lung capacity per second, and most preferably at least about 60 per cent of total lung capacity per second.

The location of the electro-magnetic induction is such that the coil will be placed directly upon the subject, up to a distance of preferably not more than 0.5 meter, more preferably less than 10 cm or 1.0 cm from the surface of the subject. As there is a linear effect to the electro-magnetic radiation, it is desired that the coil be placed relatively close to the subject to accomplish several purposes.

First, by placing the coil close to the subject there will be little over-spray of the electro-magnetic radiation with the avoidance of stimulating other functions, such as the cardiac function. Secondly, by placing the coil relatively close to the subject, the differences in signal strength of the electro-magnetic radiation will be minimized and the output of the stimulator may be maintained at a lower intensity.

The area of the subject to be stimulated is typically the T3 through L5 nerves of the mammalian subject to thereby induce the pulmonary expiration. The area of the focus of the electro-magnetic induction is conveniently determined by locating the T3 through L5 spinous processes. The electro-magnetic induction is conducted in the region of the T3 through L5 spinous processes to consequently stimulate the T3 through L5 nerves of the mammalian subject to thereby induce the pulmonary expiration.

For convenience, the spinous processes and the corresponding nerves which are to be stimulated are referred to interchangeably. Preferably, the electro-magnetic induction is addressed to the area between the T5 and L3 spinous processes, and most preferably from the T7 to the T12 spinous processes.

Conveniently, the mammalian subject is exposed to a field strength maximum magnetic flux of from 0.5 to 10.0 Tesla. Preferably, the field strength maximum flux of the electro-magnetic induction is from, 0.5 to 10.0 Tesla, conveniently 0.75 to 5.0 Tesla. The electro-magnetic induction device is typically operated between 50% and 100% of the maximum power or about 150 to 500 joules, preferably about 200 to 250 joules, conveniently 60% to 80% of the maximum power. The maximum radiation strength per electromagnetic induction is maintained at 0.5 to 50 microcurie per electro-magnetic induction, preferably 1 to 10 microcurie per electromagnetic induction.

The following is an exemplification of the present invention:

EXAMPLE I

A volunteer human male subject with a 6.0 liter total lung capacity is stimulated utilizing a 13.5 centimeter coil placed firmly at the T8 spinous process. The electromagnetic stimulation is for two seconds at 20 Hz at 70% intensity.

The cough function is induced with a single treatment of magnetic stimulation with loosening of the sputum or secretions in the trachea.

A second volunteer human male subject with a 6.0 liter total lung capacity is stimulated utilizing a 20 centimeter coil placed firmly at the T8 spinous process. The electro-magnetic stimulation is for two seconds at 20 Hz at 70% intensity.

The cough function of the second volunteer is induced with a single treatment of magnetic stimulation with loosening of the sputum or secretions in the trachea.

The device and method described herein is useful in the treatment of such respiratory difficulties where the subject has limited spinal nervous function such as from quadriplegia or multiple sclerosis. The method and device described herein are also useful in stimulating the respiratory inspiration in an asphyxiated subject, such as a drowning victim.

From the above description of the invention, those skilled in the art will perceive improvements, changes and modifications. Such improvements, changes and modifications within the skill of the art are intended to be covered by the appended claims.

What is claimed is:

1. A method for treating a mammalian subject to induce pulmonary expiration including the steps of exposing the mammalian subject to sufficient electromagnetic induction for a sufficient period of time to stimulate at least one of the T3 through L5 nerves of the mammalian subject to thereby induce the pulmonary expiration.

2. The method of claim 1 wherein the maximum radiation strength per electro-magnetic induction is from 0.5 to 50 microcurie per electro-magnetic induction.

3. The method of claim 1 wherein the focus of the electro-magnetic induction of the mammalian subject is between the T5 and L3 spinous processes.

4. The method of claim 1 wherein the electro-magnetic induction is employed for 0.25 to 30 seconds.

5. The method of claim 1 wherein the magnetic flux is from 0.5 to 10.0 Tesla.

6. The method of claim 1 wherein the total number of the electromagnetic inductions per minute upon the mammalian subject are from 2 to 100.

7. The method of claim 1 wherein the maximum flux of the electro-magnetic induction is from 0.75 to 5.0 Tesla.

8. The method of claim 1 wherein the induced pulmonary expiration of the mammalian subject is at a pressure of at least 10 centimeters of water.

9. The method of claim 1 wherein the electro-magnetic induction is conducted substantially at the end of a normal inspiration of the mammalian subject.

10. The method of claim 1 wherein the mammalian subject is human.

11. A method for treating a mammalian subject to induce pulmonary expiration including the steps of exposing the mammalian subject to sufficient electromagnetic induction for a sufficient period of time to simulate at least one of the T3 through L5 nerves of the mammalian subject and to thereby induce the pulmonary expiration wherein the maximum radiation strength per electro-magnetic induction is from 0.5 to 50 microcurie per electromagnetic induction and wherein the electro-magnetic induction is employed for 0.25 to 30 seconds.

12. The method of claim 11 wherein the mammalian subject is human.

13. The method of claim 11 wherein the induced pulmonary expiration of the mammalian subject is at a pressure of at least 10 centimeters of water.

14. The method of claim 11 wherein the maximum magnetic flux is less than 0.5 to 10.0 Tesla.

15. The method of claim 11 wherein the total number of the electro-magnetic inductions per minute upon the mammalian subject are from 2 to 100.

16. The method of claim 11 wherein the focus of the electromagnetic induction of the subject is between the T5 and L3 spinous processes.

17. The method of claim 11 wherein the induced pulmonary expiration is a cough.

18. A device for treating a mammalian subject to induce pulmonary expiration comprising:

a functional electromagnetic stimulator;

said functional electromagnetic stimulator having at least one coil wherein the coil has means to permit said coil to be hand held on the mammalian subject;

said coil having cooling means, for when the functional electro-magnetic stimulator is operating to induce pulmonary expiration, to conduct heat generated in the coil from the coil.

19. The device of claim 18 wherein said cooling means includes a chamber proximate to said coil, said chamber for receiving a fluid for cooling said coil.

20. A device for treating a mammalian subject to induce pulmonary expiration comprising:

a functional electromagnetic stimulator;

said functional electromagnetic stimulator having at least one coil wherein the coil is of a design to allow said coil to be directly placed on the mammalian subject;

said coil having cooling means, for when the functional electro-magnetic stimulator is operating to induce pulmonary expiration, to conduct heat generated in the coil from the coil.

21. The device of claim 20 wherein said cooling means includes a chamber proximate to said coil, said chamber for receiving a fluid for cooling said coil.

\* \* \* \* \*